United States Patent [19]

Zamecnik

[11] Patent Number: 5,049,550
[45] Date of Patent: Sep. 17, 1991

[54] DIADENOSINE 5', 5'''-P$^1$, P$^4$,-TETRAPHOSPHATE ANALOGS AS ANTITHROMBOTIC AGENTS

[75] Inventor: Paul C. Zamecnik, Shrewsbury, Mass.

[73] Assignee: Worcester Foundation for Experimental Biology, Mass.

[21] Appl. No.: 274,294

[22] Filed: Nov. 21, 1988

Related U.S. Application Data

[63] Continuation-in-part of Ser. No. 117,475, Nov. 5, 1987, abandoned.

[51] Int. Cl.$^5$ .................. A61K 31/70; C07H 21/02
[52] U.S. Cl. .................................. 514/47; 514/48; 514/46; 536/26; 536/27
[58] Field of Search .................. 536/27, 28; 514/47, 514/48

[56] References Cited

FOREIGN PATENT DOCUMENTS 0247819 12/1987 European Pat. Off. .
03959 1/1991 PCT Int'l Appl. .

OTHER PUBLICATIONS

Harrison, M. J. et al., "Inhibition of Platelet Aggregation and the Platelet Release Reaction by . . . Diadenosine Polyphosphates", *FEBS Letters*, 54:57-70 (1975).
Elmaleh, D. R. et al., "$^{99m}$Tc-Labeled Nucleotides as Tumor-Seeking Radiodiagnostic Agents", *Proc. Natl. Acad. Sci.*, 81:918-921 (1984).
Hollen, "Metabolism of Diadenosine Tetraphosphate (AP$_4$A)", *Hoppe-Seyler Z. Physiol. Chem.*, 365 (1984).
Luthje, J. and A. Ogilvie, "Catobolism of AP$_3$A and AP$_4$A in Human Plasma", *Eur. J. Biochem.*, 149:119-127 (1985).
Guranowski et al., "Phosphonate Analogs of Diadenosine 5',5'''-P$^1$,P$^4$ Tetraphosphate . . . ", *Biochemistry*, 26:3425-3429 (1987).
Blackburn, G. M. et al., "Synthesis and Resistance to Enzymatic Hydrolysis . . . ", *Nucleic Acids Research*, 15:6991-7004 (1987).
Zamecnik, P., (1983) *Anal. Biochem* 134:1-10.
Andersson, M., (1989) *Int. J. Biochem.* 21(7):707-714.
Louie, S., et al., (1988) *Thromb. Res.* 49:557-565.
Chao, F. C. et al., (1984) *Biochem. Biophys. Res. Comm.* 118(3):704-709.
Luthje, J. et al., (1984) *Biochem. Biophys. Res. Comm. 118(3):704-709.*
Windholz, M. et al., eds., (1983) *The Merck Index* 10:1262-1263, "8683. Streptokinase".
Hiroshi, N. et al., (1989) *Chem. Abstracts* 110(6):392, Abstract 44985u; (1988) Japanese Patent Application (kokai), Publication No. JP 6384556.
Grummt, Chemical Abstreacts, 93:165,266z, 1980.
Feldhaus et al., Chemical Abstracts, 83:159,849u, 1975.
Tarusova et al., Chemical Abstracts, 105:227,204e 1986.

*Primary Examiner*—Johnnie R. Brown
*Assistant Examiner*—L. Eric Crane
*Attorney, Agent, or Firm*—Hamilton, Brook, Smith & Reynolds

[57] ABSTRACT

A component of blood platelets analogues thereof are described. The invention is based on the discovery that this component, a dinucleotide, as well as several of its chemically synthesized analogues, is an effective antiplatelet and antithrombotic agent.

13 Claims, 4 Drawing Sheets

DIADENOSINE 5′, 5‴-P¹, P⁴,-TETRAPHOSPHATE ANALOGS AS ANTITHROMBOTIC AGENTS

GOVERNMENT SUPPORT

Work described herein was supported in part by NIH Grant GM 31562 and Cancer Center Grant 12708.

RELATED APPLICATION

This application is a continuation-in-part of U.S. Ser. No. 07/117,475, filed Nov. 5, 1987, now abandoned, the teachings of which are expressly incorporated herein by reference.

BACKGROUND OF THE INVENTION

Intravascular clotting is a common disorder. One of the most common of such disorders is the formation of thrombi, or clots which form in a blood vessel or heart cavity and remain at the point of formation. Thrombi can have serious adverse effects on an individual. For example, thrombus formation in the heart can restrict blood flow, resulting in myocardial infarction (death of the heart muscle), which is one of the most severe forms of heart attacks.

In addition to having adverse effects at the point at which it forms, all or part of a thrombus can dislodge from its point of attachment and move through blood vessels, until it reaches a point where passage is restricted and it can no longer move. The sudden blockage of blood flow which results is referred to as a thromboembolism. The lungs are particularly susceptible to emboli formation because it is in the lungs where main arteries first divide into smaller arteries and capillaries after the heart has received blood flow from the venous system. Emboli trapped in the lungs interfere with gas exchange and circulation. Accordingly, methods which prevent thrombi formation are of great medical importance.

Although the process of thrombus formation is only incompletely understood, two major stages have been identified: the aggregation of platelets at the site of a blood vessel injury, and the formation of a cross-linked fibrin polymer which binds the developing clot together.

The dinucleotide, diadenosine 5′,5‴-p¹, p⁴-tetraphosphate (AP$_4$A) (Formula I), an ubiquitous component of living cells, is stored in high concentrations in the dense granules of blood platelets Zamecnik, P. C. and Stephenson, M. L., Regulatory mechanisms for protein synthesis. In: *Mammalian Cells*, San Pietro, A., Lamborg, M. R. and Kenney, P. C. (eds.), Academic Press, New York, pp. 3–16 (1968). AP$_4$A is present in normal human platelets in a concentration higher than that present in any other cellular compartment. Flodgaard, M. and Klenow, M. *Biochemical Journal*, 208:737–742 (1983). The stored AP$_4$A was thought to be metabolically inert because incubation of platelets with $^3$H-adenosine results in labeled ATP but not labeled AP$_4$A. Thrombin treatment of platelets induces the complete release of AP$_4$A, along with other storage pool nucleotides, including ADP and the dinucleotide, diadenosine 5′,5‴-p¹, p³-triphosphate (AP$_3$A). Luthje, J. and Ogilvie, A. *Biochem. Biophys. Res. Comm.* 115:253–260 (1983). AP$_3$A is hydrolysed in plasma to AMP (adenosine monophosphate) and ADP (adenosine diphosphate); AP$_4$A is degraded to AMP and ATP (adenosine triphosphate) Luthje, J. and Ogilvie. A. *European Journal of Biochemistry*, 149:119–127 (1985).

The precise physiological role of AP$_4$A has not been defined, but it has been associated with a variety of cellular metabolic events. Zamecnik, P. *Anals of Biochemistry*, 134:1–10 (1983). The unusually high concentration of AP$_4$A in platelets has led to speculation that it has a role in platelet physiology. Platelets stimulated to undergo aggregation show a second phase of aggregation upon the release of endogenous ADP stored in the dense granules. In vitro experiments have demonstrated that AP$_4$A competitively inhibits ADP induced platelet aggregation, causing an immediate dispersion of aggregated platelets, even when aggregation has progressed to 60% completion. Chao, F. C. and Zamecnik, P., *Hoppe Seyler's Z. Physiol. Chem.*, 365:610 (1984). By contrast, AP$_3$A causes a gradual aggregation of platelets, most likely through its degradation product, ADP. The aggregating activity of AP$_3$A is immediately reversible upon the addition of AP$_4$A. Luthje, J. and Ogilvie, A. *Biochem. Biophys. Res. Comm.*, 118:704–709 (1984).

SUMMARY OF THE INVENTION

This invention is based on the discovery that administration of the dinucleotide AP$_4$A or an analogue thereof results in inhibition of platelet aggregation and reduction in thrombus formation. This invention relates to AP$_4$A and analogues of AP$_4$A, such as a $\beta$-$\beta'$-monochloro methylene derivative, E$_{10}$, and their use as antithrombotic agents in, for example, the prevention of coronary and cerebrovascular thromboembolic events, and in the prevention of thrombosis in hemodialysis arteriovenous shunts.

The present invention relates to a method for the prevention of thrombi formation which relies on the inhibition of platelet aggregation. It further relates to formulations for therapeutic use in vivo, composed of analog of Ap$_4$A, alone or in conjunction with a thrombolytic agent analogues.

DETAILED DESCRIPTION OF THE INVENTION

The subject invention relates to the use of diadenosine 5′,5′′′-p¹,p⁴-tetraphosphate (AP₄A), or an analogue thereof, as an antithrombotic agent. The invention is based on the discovery that the administration of exogenous AP₄A, or an analogue thereof, to a mammal inhibits platelet aggregation, and, therefore, reduces the incidence of thrombosis.

AP₄A has the following formula:

FORMULA I

It is also possible to apply this information to the design of antithrombotic drugs; that is, AP₄A (also represented by ApppppA) can be used as a model to design similar or more efficacious agents (e.g., synthetic analogs) to be used in the prevention of blood clots. An analog is a substance that resembles another in structure. An analog of AP₄A may have a modification in one or more of the rings of AP₄A, in one or more of substituents of AP₄A, such as an internucleotide phosphate, or in both. Examples of AP₄A analogs include App(CHCl)ppA (designated $E_{10}$), App(CHF)ppA (designated $E_5$), App(CH₂)ppA (designated $E_2$), App(CHBr)ppA, Appp(CH₂)pA, Ap(CH₂)pp(CH₂)pA (designated $E_4$), (Sp,Sp)Ap$_s$pCH₂pp$_s$A, (Rp,Rp)Ap$_s$pCH₂pp$_s$A, (Rp,Sp)Ap$_s$pCH₂pp$_s$A and additional analogs described by Blackburn et al. in *Nucleic Acid Research* 15: 6991, 1987, the teachings of which are incorporated herein by reference. Applicants have demonstrated that the β-β′-monochloromethylene derivative of AP₄A (designated $E_{10}$) is a potent inhibitor of platelet aggregation. The analogue $E_{10}$ (diadenosine chloromethylene tetraphosphate) has the formula:

For purposes of the present invention, the term "AP₄A" includes the structure shown in Formula I and all functional equivalents thereof. An analog of AP₄A is AP₄A having a modification in one or more rings, in one or more of its substituents, or in both.

AP₄A has been shown to markedly inhibit ADP-induced platelet aggregation when it is administered to a mammal. Added before or during aggregation, exogenous AP₄A blunts the secondary wave response and causes rapid dispersion of aggregated platelets. The magnitude of inhibition has been shown to bear a direct relationship to the dose of exogenous AP₄A. Because platelet plugs form the bulk of arterial thrombi, a preferred therapeutic strategy to prevent thrombosis may be to utilize a therapeutic agent (e.g., AP₄A, or an analog of AP₄A) that interferes with the adherence of platelets to vessel walls and to each other. Thus, in one embodiment of this invention, AP₄A, or one of its analogs (e.g. $E_{10}$ or $E_5$), inhibits thrombus formation when clinically administered to a mammal in need thereof.

AP₄A has a short half-life in rabbit blood, both in vivo and ex vivo (platelets obtained from the blood of subjects who have received AP₄A). Compared to in vivo clearance, the ex vivo decay of AP₄A is significantly longer. This may be explained by the use of citrated blood, which has been shown to inhibit the metal-ion dependent hydrolase responsible for the catabolism of AP₄A. Luthje, J. and Ogilvie, A., *European Journal of Biochemistry*, 149:119-127 (1985). This discovery is consistent with the previous observation that 90% of ³²P-labeled AP₄A added to normal plasma is degraded in 10 minutes when incubated at 37° C. Kim et al., *Blood*, 66:735-737 (1985). Endogenous platelet AP₄A, released in relatively high concentrations from the dense granules when stimulated platelets undergo the release phenomenon, may be important in modulating local platelet aggregation-dispersion. Thus, as described in the Example 1, an antithrombotic effect can be obtained by maintaining a high circulating AP₄A level via the administration of exogenous AP₄A. This observation suggests that AP₄A or an analog thereof, such as $E_{10}$, can be used as a clinical anti-platelet, antithrombotic agent.

AP₄A, $E_{10}$ or other analogues may be used in the prevention of coronary and cerebrovascular thromboembolic events. Because thrombi occur primarily in the arterial system, a preferred use of AP₄A or $E_{10}$ is in the treatment of patients with a high risk of arterial thrombi in the heart and brain. In addition, AP₄A may be used in hemodialysis, in which patients are linked to artificial kidney machines, to prevent thrombosis in ateriovenous shunts. Furthermore, it is possible that AP₄A or an analog thereof, such at $E_{10}$, can be employed as a secondary prophylactic agent given to help prevent the recurrence of myocardial infarctions, strokes, and venous thrombosis when present in an amount sufficient to inhibit platelet aggregation.

In general, AP₄A, or one of its analogs which inhibit platelet aggregation such as $E_{10}$, can be administered intraperitoneally, intramuscularly, subcutaneously or via slow release encapsulation. However, the preferred method of administration is by intravenous injection. AP₄A or an analog thereof can be introduced into the blood stream at any convenient point, although injection upstream from and near to the site of the suspected or known thrombus is preferred. An effective antithrombotic amount of AP$_4$A or an analog thereof is that quantity which will prevent the formation of a thrombus. The actual quantity of AP$_4$A given in a specific case will vary according to the specific compound being utilized, the particular compositions formulated, the method of administration and the clinical needs of the patient. However, the dosage of this therapeutic agent generally is 0.01 to 10 mg/kg/day.

The therapeutic agents of the present invention, can be administered by injection in conjunction with a pharmacologically acceptable carrier, either alone or in combination with another drug (e.g., a thrombolytic agent). Acceptable pharmacological carriers are those which dissolve AP$_4$A or an analog thereof or hold it in suspension, and which are compatible with physiological conditions. Examples of acceptable carriers are aqueous solutions of salts or non-ionic compounds such as sodium chloride or glucose, generally at an isotonic concentration. Other drugs may be present in the solution with AP$_4$A; it is important that such additional components do not interfere with the ability of AP$_4$A to inhibit platelet aggregation. Those skilled in the art will know, or will be able to ascertain with no more than routine experimentation, particular pharmacological carriers for said composition.

The term drug is used in this description in its broadest sense and covers drugs useful to any mammal, including but not limited to, human beings, household animals and farm animals. The term drug is further used in describing this invention as including, but is not limited to, therapeutic drugs, diagnostic drugs and preventative drugs. A variety of classes, subclasses and specific examples of drugs not expressly mentioned herein are within the scope of this invention, and these other drugs will be well known or easily ascertainable to those skilled in the art.

In another embodiment of this invention, AP$_4$A, or one of its analogs, may inhibit a thrombus from growing by preventing the further aggregation of platelets at the periphery of the existing thrombus.

In yet another embodiment of this invention, coadministration of AP$_4$A, or one of its analogs, such as E$_{10}$, which inhibit platelet aggregation, may assist also in the dissolution of existing thrombi or emboli by thrombolytic agent such as tissue plasminogen activator (TPA), streptokinase, or urokinase. For the purposes of this invention, the definition of co-administering includes (1) the simultaneous administration of AP$_4$A, or one of its analogs, and the thrombolytic agent and (2) the administration of AP$_4$A or one of its analogs, shortly before or after the administration of the thrombolytic agent. Administration in this manner of AP$_4$A or one of its analogues will result in dispersion and/or prevention the reaggregation of platelets that are released from the blood clot in response to the action of the thrombolytic agent. Since AP$_4$A, or analogues thereof, act at a very early stage in thrombus formation, they are particularly useful when combined with clot-dissolving drugs currently available.

AP$_4$A may be used in veterinary medicine. In such cases, AP$_4$A is preferably isolated from the same species of animal in which it is used, although cross-species use may be possible. In general, use in animals and humans is similar, although some variation in dosage requirements between species is expected.

The invention is illustrated further by the following examples, which are not to be taken as limiting in any way.

EXAMPLE 1

Demonstration Of The Effects Of AP$_4$A On Blood Clotting

Methods and Materials

Animal Model of Arterial Thrombosis

In previous scientific reports, it was shown in a rabbit model that clot formation in a intracarotid cannula can be modified by the administration of platelet aggregation antagonists such as suloctidil, aspirin and dipyridamole. Gurewich, V. and Lipinski, B. *Thrombosis Research,* 9:101 (1976); Louie, S. and Gurewich, V. *Thrombosis Research,* 30:323–335 (1983). The same model was used in demonstrating the antithrombotic activity of exogenous AP$_4$A.

Male, New Zealand white rabbits, weighing 2–2.5 kg., were anesthetized with ketamine hydrochloride (100 mg/kg intramuscularly). AP$_4$A (Boehringer (100 Mannheim Biochemicals, Indianapolis, Ind.), or saline control was infused via a marginal ear vein. A segment of the left common carotid artery was isolated by vascular clamps. A 1 cm. length of polyethylene tubing (PE-90, Clay Adams, Parsippany, N.Y.) was inserted, secured by silk ligatures, and the blood flow re-established by removing the clamps. Blood was sampled from the right carotid artery for assays of AP$_4$A and ATP, and for platelet aggregation studies.

After preliminary trials, a standard AP$_4$A infusion protocol was established as follows: A dose of AP$_4$A at 50 mg/kg was reconstituted in 10 ml of normal saline and infused by pump at a uniform rate over two hours. Control rabbits received 10 ml of saline alone. The intracarotid cannula was inserted, and the re-establishment of blood flow timed at 15 minutes into the infusion. Upon the completion of infusion at 2 hours, the intracarotid tubing was removed, and its contents flushed out into a petri dish. The presence of a clot or of liquid blood contents was noted.

To avoid possible bias by minor changes in surgical technique, all the animal work was performed by the same operator; rabbits were assigned to experimental or control groups at random.

Assay of Blood AP$_4$A and ATP

Blood samples were collected from the carotid artery through a catheter before and after (0, 10, 20, 40, and 60 minutes) infusion of AP$_4$A. Blood was anticoagulated by mixing with 0.15 volume of acid-citrate-dextrose solution. An aliquot of blood collected at the end of AP$_4$A infusion (t$_o$ sample) was incubated at 37° C. and sampled at 10, 20, 40, and 60 minutes to evaluate the in vitro decay of AP$_4$A. Blood samples of 115 ul each were admixed rapidly with 1.885 ul 3% perchloric acid and kept at 0° C. for 30 minutes with intermittent vortexing. The acid soluble fraction was recovered by centrifugation at 1000 g for 10 minutes and neutralized by 5M K$_2$CO$_3$. It was then kept at −80° C. until assay of the nucleotides. The AP$_4$A assay was performed by coupling the phosphodiesterase and luciferase reactions in a luminometer (Model 6100 Picolite, Packard, Downers Grove, Ill.). The detailed method of AP$_4$A and ATP assays has been reported elsewhere (Kim, B. K., Chao, F. C., Leavitt, R., Fauci, A. S., Meyers, K. M. and Zamecnik, P. C. *Blood,* 66:735–737, 1985).

Platelet Aggregation Studies

Rabbit carotid arterial blood was collected in 3.8% sodium citrate (9 volumes blood to 1 volume citrate). Platelet rich plasma (PRP) and platelet poor plasma (PPP) were prepared by centrifugation at 150 g and 1,000 g for 10 minutes respectively. Aggregation studies were performed in a Chrono-Log (Havertown, Pa.) aggregometer with ADP or collagen as aggregating agents. ADP (Sigma Chemical Co.) was used in a final concentration of $2 \times 10^{-5}$M. Calf skin collagen (Sigma Chemical Co.) was used in a final concentration of 200 ug/ml.

Experimental Design and Statistical Analysis

Twenty-five rabbits each were assigned to the experimental group that received $AP_4A$ (50 mg/kg), and the control group that received normal saline alone. The incidence of clot formation in the intracarotid cannula in the two groups was compared by the Chi-Square test.

Blood Levels of $AP_4A$ and ATP

The disappearance of infused $AP_4A$ in the circulation and in incubated blood was studied in 2 rabbits. Mean values of hemoglobin, hematocrit and platelet count were 10.1 g/dl, 30.8% and 362,000/ul respectively. The blood content of $AP_4A$ in the rabbits was 51 nmol/l blood prior to infusion. This was 7.3 fold lower than the level observed in man, and comparable to the levels of $AP_4A$ in the platelets of cats and cattle. Kim, B. K. et al., *Blood*, 66:735-737 (1985); Flodgaard, H., Zamecnik, P. C. Meyers, K. and Klenow, H., *Thrombosis Research*, 37:345-351 (1986). At the end of infusion it had increased to 125 fold of baseline (6.4 u mol/l blood). A very rapid disappearance of infused $AP_4A$ was observed, with complete clearance within 10 minutes after infusion. When blood samples obtained at the end of $AP_4A$ infusion were incubated at 37° C., only 15-fold and 4-fold levels of $AP_4A$, as compared to baseline could be detected after 10 minutes and 20 minutes respectively. The results indicated that the ex vivo decay is slightly longer than the in vivo clearance. On the other hand, the level of ATP showed bimodal increments: an initial increment and a late increment (Table 1).

The increased ATP level in the blood obtained at the end of $AP_4A$ infusion may reflect an increase in plasma ATP, an immediate degradation product of $AP_4A$, plus an increase in blood cell ATP, generated from adenosine produced by $AP_4A$ degradation during the 2 hours of infusion. A late increment of ATP at 60 minutes is most likely due to the result of increased intracellular ATP. These observations indicate that blood plasma contains a considerable amount of phosphomonoesterase as well as phosphodiesterase activity. The diminished response to ADP-induced aggregation seen in platelets recovered from $AP_4A$-infused rabbits was probably due to the combined effects of $AP_4A$ and its degradation products such as ATP, AMP and adenosine.

The Effect of $AP_4A$ on Platelet Aggregation

Figure 1:
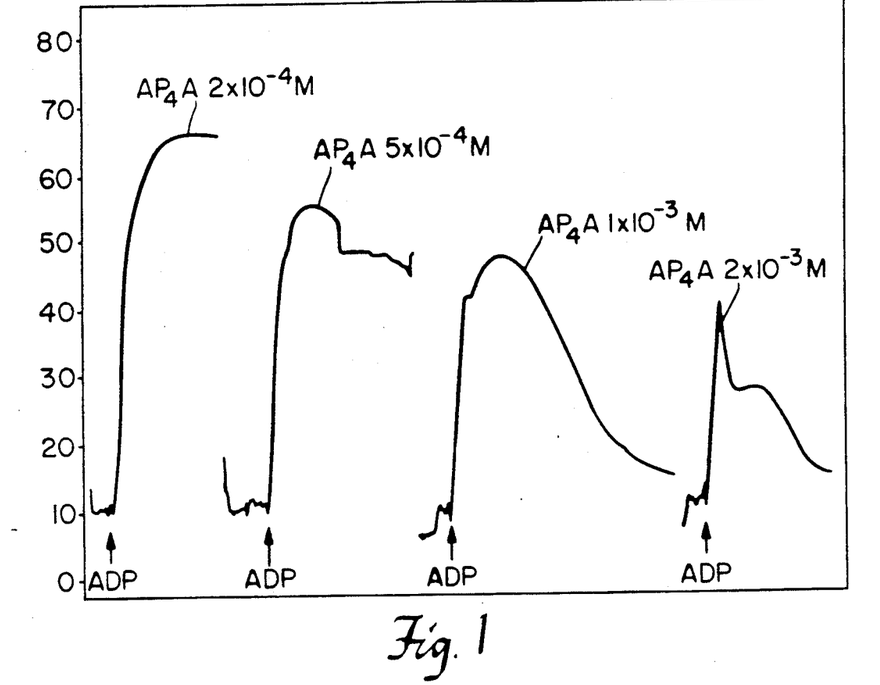
FIG. 1 is a graph showing the effect of AP$_4$A on platelet aggregation induced by $2 \times 10^{-5}$M ADP when AP$_4$A is added at the midpoint of the ADP-induced secondary wave aggregation.
Figure 2:
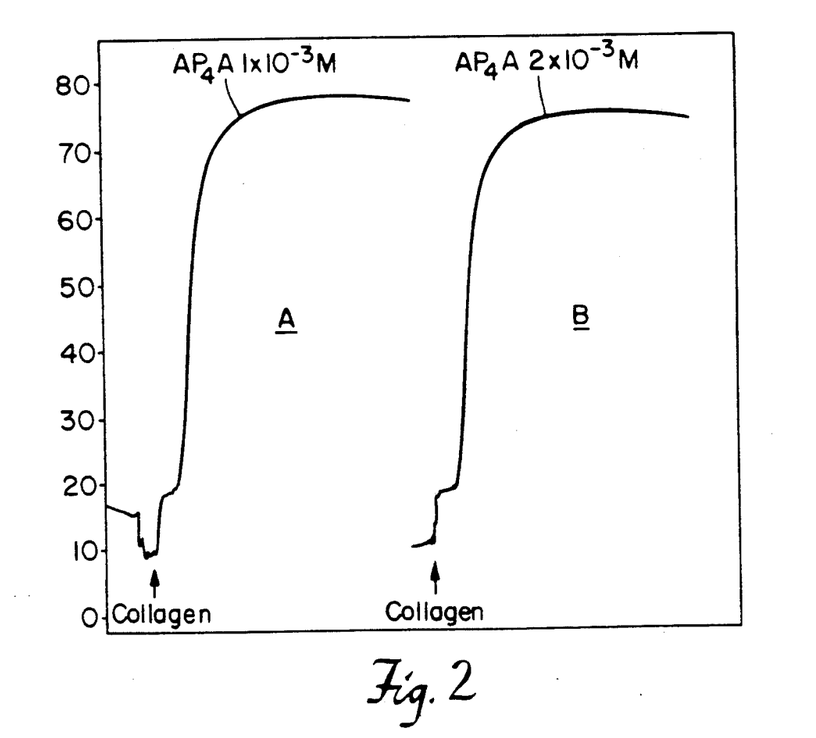
FIG. 2 is a graph showing the effect of AP$_4$A (Panel A, $1 \times 10^{-3}$M, Panel B, $2 \times 10^{-3}$M) on platelet aggregation induced by collagen (200 $\mu$g/ml) when AP$_4$A is added at the peak of collagen-induced aggregation.
Figure 3:
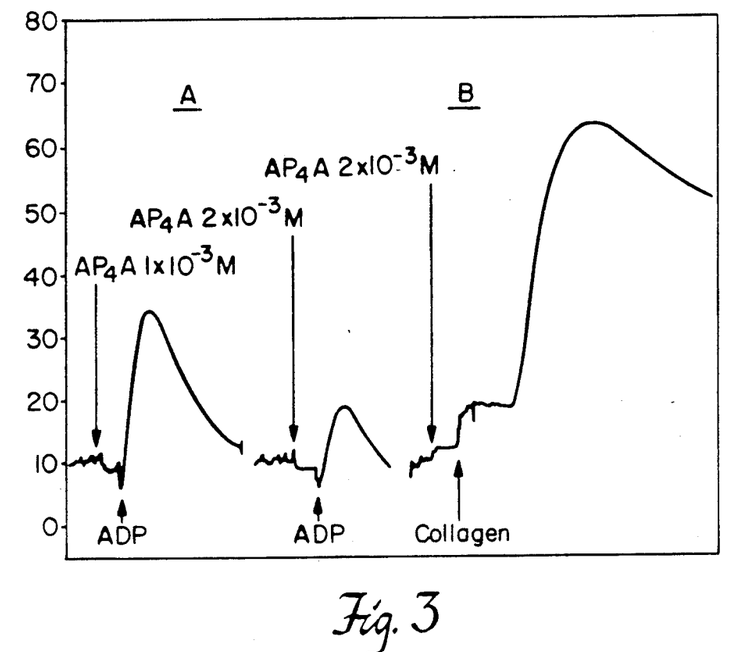
FIG. 3 shows the effect of AP$_4$A on platelet aggregation. Panel A is a graph showing the effect of AP$_4$A on platelet aggregation induced by $2 \times 10^{-5}$M ADP when the AP$_4$A is added before the ADP. Panel B is a graph showing the effect of AP$_4$A on platelet aggregation induced by collagen (200 $\mu$g/ml), when the AP$_4$A is added before the collagen.

The effect of $AP_4A$ on rabbit platelet aggregation by ADP and collagen was tested. Both ADP ($2 \times 10^{-5}$M) and collagen (200 ug/ml) caused prompt and complete platelet aggregation, with a small primary wave and a sustained secondary wave of aggregation. Addition of $AP_4A$ during aggregation blunted the secondary wave response to ADP and caused the dispersion of aggregated platelets. The anti-aggregatory effect of $AP_4A$ was detected at a concentration of $2 \times 10^{-4}$M (tenfold that of ADP) and increased in a dose-response pattern with increasing concentrations (FIG. 1). Similar results were obtained when $AP_4A$ was added immediately before the initiation of aggregation by ADP (FIG. 3A). However, $AP_4A$, while inhibiting slightly the collagen-induced aggregation when added prior to the induction of aggregation (FIG. 3B), had no effect on the dispersion of preformed aggregates caused by collagen (FIG. 2). Thus, the same dose of $AP_4A$ that causes almost complete inhibition of ADP-induced aggregation has little or no effect on collagen-induced platelet aggregation.

Figure 4:
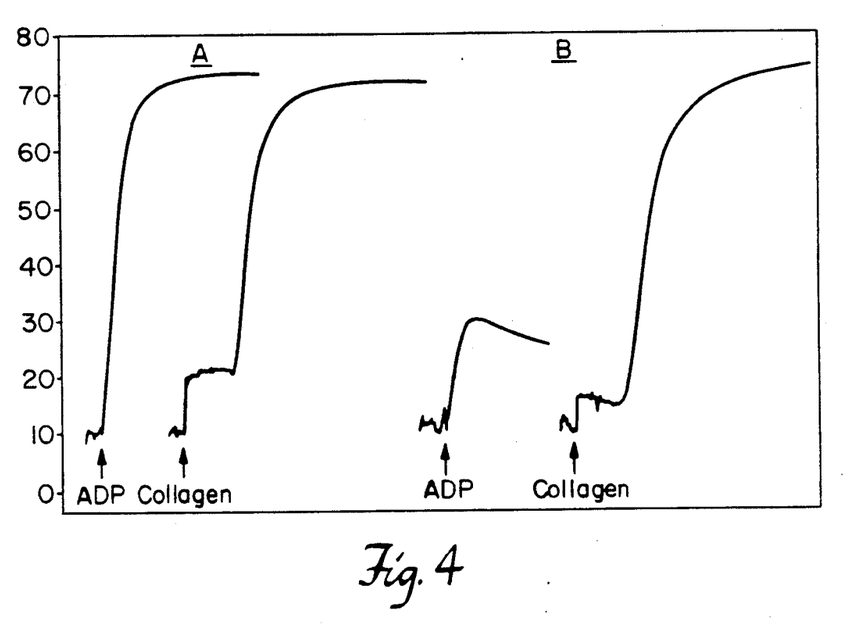
FIG. 4 is a graph showing the aggregation of platelets recovered from control (Panel a) and AP$_4$A-treated (Panel b) rabbits induced by ADP ($2 \times 10^{-5}$M) and collagen (200 $\mu$g/ml).

FIG. 4 shows the results from platelet aggregation studies performed on blood from two rabbits receiving saline (Panel a) or $AP_4A$ (Panel b) infusion. At an infusion dose of 50 mg per kg over 2 hours, $AP_4A$ markedly blunted the aggregation of platelets induced by ADP ($2 \times 10^{-5}$M), but had little effect on collagen-induced (200 ug/ml) aggregation.

TABLE 1

Blood Contents of ATP and $AP_4A$ in Rabbits: (Before and After Infusion of $AP_4A$)

| | ATP, umol/l blood | | $AP_4A$, umol/l blood | |
|---|---|---|---|---|
| | in vivo | ex vivo | in vivo | ex vivo |
| Before infusion | 522.9 | — | 0.051 | — |
| After infusion, | | | | |
| 0 min | 579.0 | — | 6.406 | — |
| 10 | 573.5 | 570.1 | 0.043 | 0.799 |
| 20 | 564.0 | 559.3 | 0.045 | 0.210 |
| 40 | 562.0 | 551.5 | 0.050 | 0.041 |
| 60 | 629.5 | 572.0 | 0.042 | 0.037 |

The Effect of $AP_4A$ Infusion on Thrombosis

Twenty-five rabbits received a constant infusion of $AP_4A$ at a total dose of 50 mg/kg over 2 hours. Twenty-five control rabbits received saline infusion alone. The presence or absence of a clot in the intracarotid cannula was noted at the end of 2 hours. Of the 25 rabbits that received $AP_4A$, 14 were found to have formed clots in the intracarotid cannula, giving an incidence of thrombosis of 56%. Among the 25 saline controls, there were 21 clots, the incidence of thrombosis in the controls being 84% (p 0.05, Chi-Square test) (Table 2). The morphology of the intra-cannular thrombi has been described previously. Louie, S. and Gurewich, V. *Thrombosis Research*, 30:323-335 (1983). They consisted of a red body and a white head attached to the proximal or distal end of the cannula. Microscopically, large masses of platelets were separated by bands of fibrin, with other sections showing packed red cells and fibrin. There was no significant difference in dimension and weight between the clots found in the $AP_4A$-infused rabbits and those recovered from the controls.

TABLE 2

| TREAT-MENT | TOTAL RABBITS | CLOT PRESENT | CLOT ABSENT | % CLOTS | P |
|---|---|---|---|---|---|
| $AP_4A$ | 25 | 14 | 11 | 56 | 0.05 |
| Saline | 25 | 21 | 4 | 86 | |

EXAMPLE 2

Demonstration Of The Effects Of Analogues of $AP_4A$ On Blood Clotting

This Example illustrates that $AP_4A$ analogues, especially the analogue designated as $E_{10}$, are potent inhibitors of platelet aggregation and blood clot formation.

Inhibition Of Platelet Aggregation By $AP_4A$ Analogues

Human platelet-rich plasma was pre-incubated at 37° C. with the appropriate analogue for 1 minute. Aggregation was then induced by 5 μM ADP. ID$_{50}$ values (i.e. concentration of analogue at which platelets are inhibited by 50 percent) were obtained from log-dose response plots. Results showed that there is a wide-variation in inhibition of ADP-induced platelet aggregation among the analogues of AP$_4$A used (Table 3).

TABLE 3

Inhibitory Effects (ID50) Of Various Analogues Of Ap$_4$A on ADP-Induced Platelet Aggregation.

| Analogue Designation | Agents | ID50, μM |
|---|---|---|
| E$_1$ | Ap(CH$_2$)pp(CH$_2$)pA | >50 |
| E$_2$ | App(CH$_2$)ppA | 22 |
| E$_3$ | App(CH$_2$)$_2$ppA | 11 |
| E$_4$ | Ap(CH$_2$)pp(CH$_2$)pA | >50 |
| E$_5$ | App(CHF)ppA | 4 |
| E$_6$ | Ap(CHF)pp(CHF)pA | 50 |
| E$_7$ | Ap(CF$_2$)pp(CF$_2$)pA | 15 |
| E$_8$ | App(CF$_2$)ppA | 6 |
| E$_9$ | Ap(CHCl)pp(CHCl)pA | 19 |
| E$_{10}$ | App(CHCl)ppA | 3 |
| E$_{11}$ | Ap(CCL$_2$)pp(CCl$_2$)pA | 9 |
| E$_{12}$ | App(CCl$_2$)ppA | 10 |

Use of biphosphonate analogues having P-C-P bridges located in the P$^2$-P$^3$ position resulted in greater inhibition than observed with other analogues. For example, the β-β'-monochloromethylene derivative of AP$_4$A designated E$_{10}$ (App(CHCl)ppA) was particularly effective, as was a monofluoro derivative, E$_5$ (App(CHF)ppA).

Figure 5:
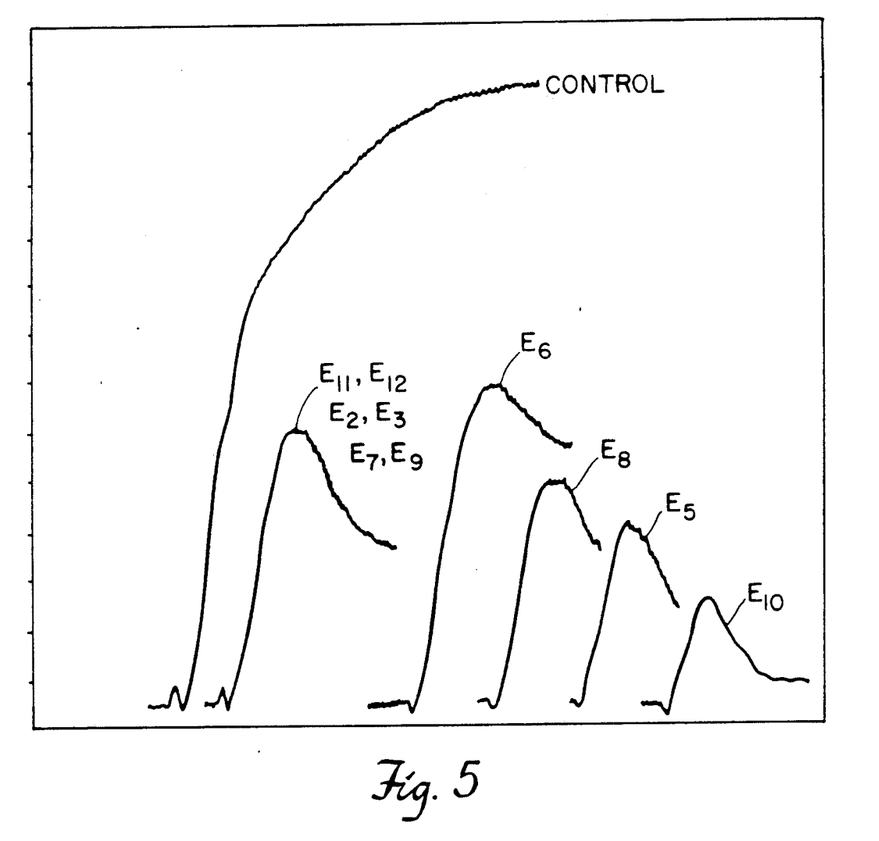
FIG. 5 is a graphic representation of ADP-induced aggregation of platelets in the presence of various inhibitor analogues of AP$_4$A.

FIG. 5 is a graphic representation of the data. FIG. 5 shows aggregation of platelets in platelet-rich medium from human blood, in the presence of 5 μM ADP. The inhibitor analogues (12.5 μM) numbered 1–12 are cross-referenced to the analogues numbered in Table 3.

Under the conditions used, the β-β'-monochloromethylene analogue of AP$_4$A (E$_{10}$) was the most effective inhibitor of platelet aggregation. The monofluoro analogue (E$_5$) was the next most effective in inhibiting platelet aggregation. Analogues E$_1$ and E$_4$ showed no effect on platelet inhibition, even at 50 μM.

The Effect Of E$_{10}$ Infusion On Thrombosis

Initially, twelve rabbits received a constant infusion of E$_{10}$ over a 2 hour period at a dosage of 100 mg in 10 ml. These intravenous infusions were performed as described above for AP$_4$A.

In addition, 30 mg of E$_{10}$ in 3 ml saline was administered as a single injection over a one minute time span at the beginning of the cannulation period. Results are given in Table 4.

TABLE 4

Inhibitory Effects Of Diadenosine Chloromethylene Tetraphosphate On Intracarotid Artery Thrombosis

| Treatment | Total No. Rabbits | Clot Present | Clot Absent | % Clots | P |
|---|---|---|---|---|---|
| E$_{10}$ (100 mg) | 12 | 4 | 8 | 33 | 0.05 |
| (30 mg) | 6 | 2 | 4 | 33 | 0.05 |
| Total | 18 | 6 | 12 | 33 | 0.025 |
| Saline Control | 15 | 12 | 3 | 80 | — |

As shown in Table 4, two-thirds of the injected rabbits (8 rabbits) showed no incidence of clotting. The Chi-square test shows this anti-thrombotic effect to be significant (p<0.05). The E$_{10}$ treatment at the 30 mg level shows a similar response but the sample size is too small to reveal a statistically significant effect of E$_{10}$ on clot formation. When combined with the 100 mg series, the data show that E$_{10}$ significantly reduces clot formation, as compared to saline controls.

Competitive Inhibition of ADP-Induced Platelet Aggregation By E$_{10}$

Figure 6:
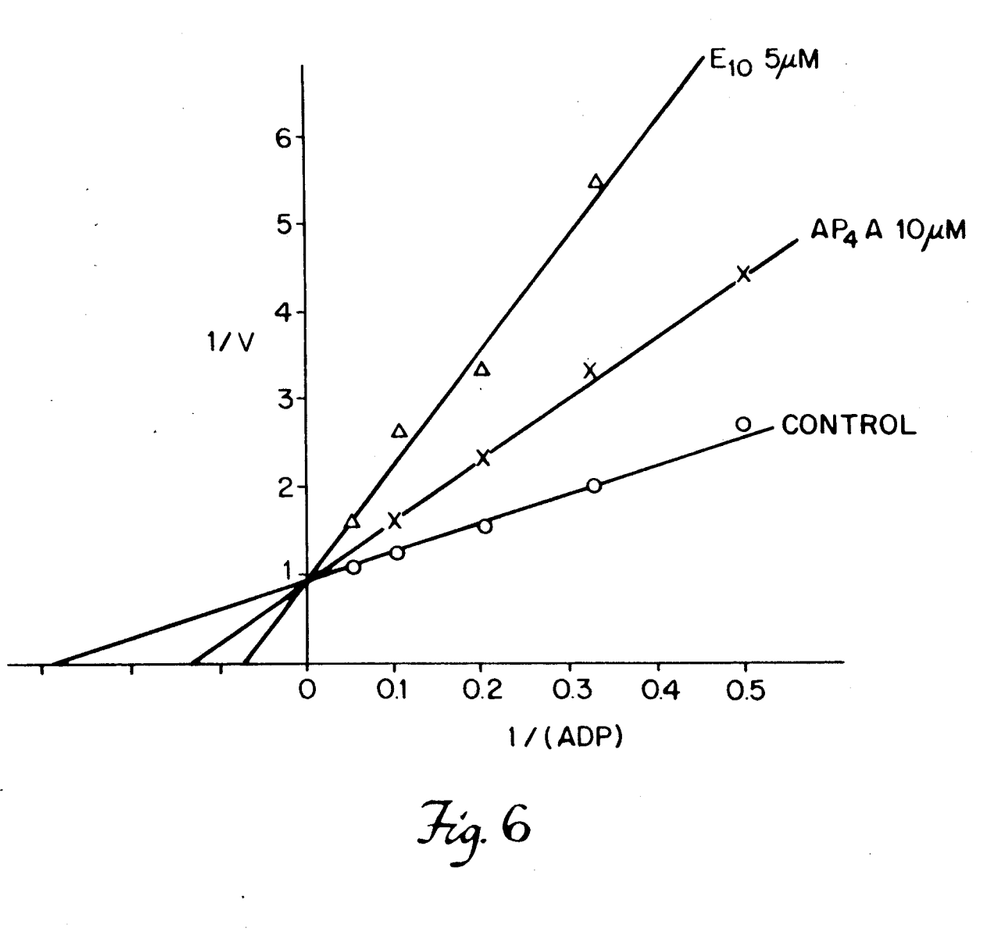
FIG. 6 is a double-reciprocal plot showing the inhibitory effect of AP$_4$A and E$_{10}$ upon ADP-induced platelet aggregation.

Changes in light transmission reflecting the velocity of ADP-induced platelet aggregability was determined using a platelet aggregometer. Born, G.V.P., Nature 184:927–929 (1962). When the reciprocal of velocity (1/v) is plotted against the reciprocal of substrate (i.e. ADP) concentration, the inhibitory effects of AP$_4$A and E$_{10}$ are revealed (FIG. 6). The kinetic plot is characteristic of competitive inhibition; in this double reciprocal plot only the slope is affected by the presence of inhibitor (AP$_4$A or E$_{10}$), the Y-intercepts remain constant. The Y points on the X-intercept are altered by factors $$\left(1 + \frac{I}{K_i}\right)$$

where I is the concentration of inhibitor, and K$_i$ is a characteristic constant. Points on the X-intercept are given by the expression $$\frac{-1}{K_m} / \left(1 + \frac{[I]}{K_i}\right)$$

intercept when [I]=0. When [I] is known, the equation can be solved for K$_i$. In this Figure, the K$_m$ for ADP is 3.0 μM, the K$_i$ for AP$_4$A is 17.1 μM and 6.7 μM for E$_{10}$. This figure shows that E$_{10}$ is superior to AP$_4$A as a competitive inhibitor of ADP-induced platelet aggregation.

EXAMPLE 3

The Effect of Sulfur-Containing AP$_4$A Analogues on Platelet Aggregation

This Example illustrates that sulfur-containing analogues of AP$_4$A are as effective as E$_{10}$ in inhibiting aggregation of platelets. Platelet aggregation was induced by ADP and its inhibition measured as in the previous Example. Results show that sulfur-containing (i.e., those containing thiophosphate and thiophosphonate linkages) AP$_4$A analogues. E$_{13}$ and E$_{15}$, have an inhibitory effect as great as E$_{10}$ (Table 5).

TABLE 5

Effect of Sulfur-Containing AP$_4$A Analogues on ADP-Induced Blood Platelet Aggregation

| Analogue Designation | Agents | ID50, μM |
|---|---|---|
| E$_{10}$ | App(CHCl)ppA | <5 |
| E$_{13}$ | Ap$_s$p(CHF)pp$_s$A | 7 |
| E$_{14}$ | Ap$_s$p(CF$_2$)pp$_s$A | 17 |
| E$_{15}$ | Ap$_s$ppp$_s$A | 6 |

Equivalents

Those skilled in the art will recognize, or be able to ascertain using no more than routine experimentation, many equivalents to the specific embodiments of the invention described herein. Such equivalents are intended to be encompassed by the following claims.

I claim:

1. In a method for dissolving a thrombus in a mammal in need thereof wherein a thrombolytic agent is administered to said mammal, the thrombolytic agent selected from the group consisting of:

tissue plasminogen activator, streptokinase and urokinase, the improvement comprising coadministering to said mammal an effective thrombolytic amount of a thrombolytic agent in conjunction with an effective antithrombotic amount of an analog of Ap$_4$A or an analog thereof, the analog selected from the group consisting of:

App(CH$_2$)ppA, App(CH$_2$CH$_2$)ppA, App(CHF)ppA, App(CF$_2$)ppA, Ap$_s$p(CHF)pp$_s$A, Ap$_s$p(CF$_2$)pp$_s$A, Ap(CF$_2$)pp(CF$_2$)pA, App(CHCl)ppA, App(CCl$_2$)ppA, Ap(CHCl)pp(CHCl)pA, Ap(CCl$_2$)pp(CCl$_2$)pA, and Ap$_s$ppp$_s$A.

2. A method for inhibiting the growth of an existing thrombus in a mammal in need thereof, comprising administering to said mammal a quantity of an analog of diadenosine 5′,5′′′-p$^1$,p$^4$-tetraphosphate, effective for inhibiting a platelet aggregation, the analog selected from the group consisting of:

App(CH$_2$)ppA, App(CH$_2$CH$_2$)ppA, App(CHF)ppA, App(CF$_2$)ppA, Ap$_s$p(CHF)pp$_s$A Ap$_s$p(CF$_2$)pp$_s$A, Ap(CF$_2$)pp(CF$_2$)pA, App(CHCl)ppA, App(CCl$_2$)ppA, Ap(CHCl)pp(CHCl)pA, Ap(CCl$_2$)pp(CCl$_2$)pA, and Ap$_s$ppp$_s$A.

3. A method of reducing the formation of a thrombus in a mammal in need thereof by inhibiting platelet aggregation, comprising administering to said mammal an effective antithrombotic amount of an analog of diadenosine 5′,5′′′-p$^1$,p$^4$-tetraphosphate, the analog selected from the group consisting of:

App(CH$_2$)ppA, App(CH$_2$CH$_2$)ppA, App(CHF)ppA, App(CF$_2$)ppA, Ap$_s$p(CHF)pp$_s$A, Ap$_s$p(CF$_2$)pp$_s$A, Ap(CF$_2$)pp(CF$_2$)pA, App(CHCl)ppA, App(CCl$_2$)ppA Ap(CHCl)pp(CHCl)pA, Ap(CCl$_2$)pp(CCl$_2$)pA, and Ap$_s$ppp$_s$A.

4. A method of inhibiting platelet aggregation in a mammal in need thereof, comprising administering to said mammal an effective amount of an analog of diadenosine 5′,5′′′-p$^1$,p$^4$-tetraphosphate, the analog selected from the group consisting of:

App(CH$_2$)ppA, App(CH$_2$CH$_2$)ppA, App(CHF)ppA, App(CF$_2$)ppA, Ap$_s$p(CHF)pp$_s$A, Ap$_s$p(CF$_2$)pp$_s$A, Ap(CF$_2$)pp(CF$_2$)pA, App(CHCl)ppA, App(CCl$_2$)ppA, Ap(CHCl)pp(CHCl)pA, Ap(CCl$_2$)pp(CCl$_2$)pA, and Ap$_s$ppp$_s$A.

5. A method for inhibiting the growth of an existing thrombus in a mammal in need thereof, comprising administering to said mammal an effective antithrombotic amount of an analog of diadenosine 5′,5′′′-p$^1$,p$^4$-tetraphosphate, the analog selected from the group consisting of:

App(CHBr))ppA, Appp(CH$_2$)pA, Ap(CH$_2$)pp(CH$_2$)pA, Ap$_s$p(CF$_2$)pp$_s$A, Ap$_s$ppp$_s$A, Ap(CH$_2$)ppA, App(CH$_2$CH$_2$)ppA, App(CHF)ppA, App(CF$_2$)ppA, App(CHCl)ppA, App(CCl$_2$)ppA, Ap$_s$p(CHF)pp$_s$A, Ap(CHCl)pp(CHCl)pA, Ap(CCl$_2$)pp(CCl$_2$)pA, and Ap(CF$_2$)pp(CF$_2$)pA.

6. A method for inhibiting or reducing the formation of a thrombus in a mammal in need thereof, comprising administering to said mammal an effective amount of the pharmaceutical composition of claim 2, thereby inhibiting, preventing or reducing the formation of a thrombus.

7. In a method for dissolving an existing thrombus in a mammal in need thereof wherein an effective thrombolytic amount of a thrombolytic agent selected from the group consisting of tissue plasminogen activator, streptokinase and urokinase is administered to said mammal, the improvement comprising co administering to the mammal an effective amount of an analog of diadenosine 5′,5′′′-p$^1$,p$^4$-tetraphosphate, wherein the analog selected from the group consisting of:

App(CHF)ppA, App(CF$_2$)ppA, Ap$_s$p(CHF)pp$_s$A, Ap$_s$p(CF$_2$)pp$_s$A, Ap(CF$_2$)pp(CF$_2$)pA, App(CHCl)ppA, App(CCl$_2$)ppA, Ap(CHCl)pp(CHCl)pA, Ap(CCl$_2$)pp(CCl$_2$)pA, and Ap$_s$ppp$_s$A.

8. In an antithrombotic composition, the improvement comprising an effective antithrombotic amount of an analog of diadenosine 5′,5′′′-p$^1$,p$^4$-tetraphosphate, the analog selected from the group consisting of:

App(CH$_2$)ppA, App(CH$_2$CH$_2$)ppA, App(CHBr)ppA, Ap$_s$p(CF$_2$)pp$_s$A, Ap$_s$ppp$_s$A, App(CHF)ppA, App(CF$_2$)ppA, App(CHCl)ppA, App(CCl$_2$)ppA, Ap$_s$p(CHF)pp$_s$A, Ap(CHCl)pp(CHCl)pA, Ap(CCl$_2$)pp(CCl$_2$)pA, and Ap(CF$_2$)pp(CF$_2$)pA, and a pharmacologically acceptable carrier thereof.

9. In a pharmaceutical composition wherein the first effective ingredient is comprised of an effective thrombolytic amount of a thrombolytic agent, the thrombolytic agent selected from the group consisting of tissue plasminogen activator, streptokinase, and urokinase, the improvement comprising the coadministration of a second effective ingredient, comprised of an effective antithrombotic amount of an analog of diadenosine 5′,5′′′-p$^1$,p$^4$-tetraphosphate, the analog selected from the group consisting of:

App(CH$_2$)ppA, App(CH$_2$CH$_2$)ppA, App(CHBr)ppA, Appp(CH$_2$)pA, Ap$_s$p(CF$_2$)pp$_s$A, Ap$_s$ppp$_s$A, App(CHF)ppA, App(CF$_2$)ppA, App(CHCl)ppA, App(CCl$_2$)ppA, Ap$_s$p(CHF)pp$_s$A, Ap(CHCl)pp(CHCl)pA, Ap(CCl$_2$)pp(CCl$_2$)pA, and Ap(CF$_2$)pp(CF$_2$)pA, and a pharmacologically acceptable carrier thereof.

10. A pharmaceutical composition comprising:
a) a thrombolytic amount of a thrombolytic agent selected from the group consisting of tissue plasminogen activator, streptokinase and urokinase and
b) an antithrombotic amount of diadenosine 5′,5′′′-p$^1$,p$^4$-tetraphosphate or an analog of diadenosine 5′,5′′′-p$^1$,p$^4$-tetraphosphate.

11. The pharmaceutical composition of claim 10 wherein the analog of diadenosine 5′,5′′′-p$^1$,p$^4$-tetraphosphate, is selected from the group consisting of:

App(CHF)ppA, App(CF$_2$)ppA, Ap$_s$p(CHF)pp$_s$A, Ap$_s$p(CF$_2$)pp$_s$A, Ap(CF$_2$)pp(CF$_2$)pA, App(CHCl)ppA, App(CCl$_2$)ppA, Ap(CHCl)pp(CHCl)pA, Ap(CCl$_2$)pp(CCl$_2$)pA, and Ap$_s$ppp$_s$A.

12. An analog of Ap$_4$A effective for inhibiting formation of a thrombus in vivo, wherein the analog is selected from the group consisting of:

App(CHF)ppA, App(CF$_2$)ppA, Ap$_s$p(CHF)pp$_s$A, Ap$_s$p(CF$_2$)pp$_s$A, Ap(CF$_2$)pp(CF$_2$)pA, App(CHCl)ppA, App(CCl$_2$)ppA, Ap(CHCl)pp(CHCl)pA, Ap(CCl$_2$)pp(CCl$_2$)pA, and Ap$_s$ppp$_s$A.

13. An analog of Ap$_4$A, effective for inhibiting formation of a thrombus in vivo or in vitro, wherein the analog is selected from the group consisting of:

App(CHF)ppA, App(CF$_2$)ppA, Ap$_s$p(CHF)pp$_s$A, Ap$_s$p(CF$_2$)pp$_s$A, Ap(CF$_2$)pp(CF$_2$)pA, App(CHCl)ppA, App(CHCl)ppA, App(CCl$_2$)ppA, Ap(CHCl)pp(CHCl)pA, App(CCl$_2$)pp(CCl$_2$)pA, and Ap$_s$ppp$_s$A.

* * * * *

UNITED STATES PATENT AND TRADEMARK OFFICE
CERTIFICATE OF CORRECTION

PATENT NO. : 5,049,550
DATED : September 17, 1991
INVENTOR(S) : Paul C. Zamecnik It is certified that error appears in the above-identified patent and that said Letters Patent is hereby corrected as shown below:

Claim 1, Column 11, line 8, delete "or an analog thereof".

Claim 5, Column 11, line 54, the sixth compount should read ---App(CH$_2$)ppA---.

Claim 11, Column 12, line 48, the fifth compound should read ---Ap(CF$_2$)pp(CF$_2$)pA---.

Claim 12, Column 12, line 56, the fifth compound should read ---Ap(CF$_2$)pp(CF$_2$)pA---.

Claim 13, Column 12, line 66, the ninth group should be ---Ap(CCl$_2$)pp(CCl$_2$)pA---.

Claim 13, Column 12, line 65, the seventh group should be deleted.".

Signed and Sealed this

Twenty-fifth Day of May, 1993

Attest:

MICHAEL K. KIRK

Attesting Officer

Acting Commissioner of Patents and Trademarks